(12) United States Patent
Kipke et al.

(10) Patent No.: US 9,248,269 B2
(45) Date of Patent: Feb. 2, 2016

(54) NEURAL DEVICE WITH MODULAR ELECTRODE ARRAY

(75) Inventors: Daryl R. Kipke, Dexter, MI (US); Rio J. Vetter, Ypsilanti, MI (US); Kc Kong, Ann Arbor, MI (US); Jamille Hetke, Brooklyn, MI (US); David Anderson, Ann Arbor, MI (US)

(73) Assignee: NeuroNexus Technologies, Inc., Ann Arbor, MI (US)

( * ) Notice: Subject to any disclaimer, the term of this patent is extended or adjusted under 35 U.S.C. 154(b) by 350 days.

(21) Appl. No.: 13/556,715

(22) Filed: Jul. 24, 2012

(65) Prior Publication Data

US 2013/0144365 A1 Jun. 6, 2013

Related U.S. Application Data

(60) Provisional application No. 61/511,343, filed on Jul. 25, 2011.

(51) Int. Cl.
*A61B 5/0478* (2006.01)
*A61N 1/05* (2006.01)
(Continued)

(52) U.S. Cl.
CPC .......... *A61N 1/0476* (2013.01); *A61B 5/04001* (2013.01); *A61B 5/0478* (2013.01); *A61B 5/4064* (2013.01); *A61N 1/0502* (2013.01);
(Continued)

(58) Field of Classification Search
CPC .............. A61B 5/0478; A61B 5/0408; A61B 5/04085; A61B 5/042; A61B 5/0422; A61B 5/0492; A61B 5/40; A61B 5/4029–5/4052; A61B 5/4058–5/407; A61B 5/6846; A61B 5/6847; A61B 5/6868; A61B 5/6877; A61B 2560/04; A61B 2562/028; A61B 2562/046; A61B 2562/12; A61B 2562/125; A61B 2562/164; A61B 2562/187; A61B 2562/227; A61N 1/04; A61N 1/05; A61N 1/0529–1/0539; A61N 1/0543; A61N 1/0551–1/0558; A61N 1/0597
USPC .................. 600/373, 377, 378, 393; 607/118; 29/825
See application file for complete search history.

(56) References Cited

U.S. PATENT DOCUMENTS 4,354,508 A * 10/1982 Murfitt et al. .................. 607/152
5,897,583 A * 4/1999 Meyer et al. .................. 607/116
(Continued)

FOREIGN PATENT DOCUMENTS

WO 2005058145 6/2005
WO 2010055421 5/2010
(Continued)

OTHER PUBLICATIONS

Invitation to Pay Additional Fees to PTO, Dated Oct. 31, 2012, Application # US2012/047994.
(Continued)

*Primary Examiner* — Lee S Cohen
*Assistant Examiner* — Erin M Cardinal
(74) *Attorney, Agent, or Firm* — Michael F. Scalise

(57) ABSTRACT

An apparatus comprises a flexible substrate including a modular electrode array disposed on the flexible substrate. The modular electrode array includes a plurality of electrode modules, where an electrode module includes a plurality of electrodes. The flexible substrate also includes a spatial separation between the electrode modules of the modular electrode array, and conductive interconnect coupled to the electrodes of the plurality of electrodes.

43 Claims, 11 Drawing Sheets

(51) Int. Cl.
*A61N 1/04* (2006.01)
*A61B 5/04* (2006.01)
*A61N 1/36* (2006.01)
*A61N 5/06* (2006.01)
*A61B 5/00* (2006.01)

(52) U.S. Cl.
CPC .......... *A61N 1/0531* (2013.01); *A61N 1/36064* (2013.01); *A61N 5/06* (2013.01); *A61B 5/0059* (2013.01); *A61B 5/4094* (2013.01); *A61B 2562/0209* (2013.01); *A61B 2562/046* (2013.01); *A61N 5/0622* (2013.01); *Y10T 29/49117* (2015.01)

(56) References Cited

U.S. PATENT DOCUMENTS

| | | | | |
|---|---|---|---|---|
| 6,055,448 | A * | 4/2000 | Anderson et al. | 600/372 |
| 2002/0198582 | A1 * | 12/2002 | Edell et al. | 607/116 |
| 2005/0154435 | A1 | 7/2005 | Stern et al. | |
| 2008/0306576 | A1 * | 12/2008 | Boyden et al. | 607/91 |
| 2009/0210039 | A1 * | 8/2009 | Boyden et al. | 607/89 |
| 2009/0306485 | A1 * | 12/2009 | Bell | 600/301 |
| 2010/0198297 | A1 | 8/2010 | Cogan et al. | |
| 2010/0204560 | A1 | 8/2010 | Salahieh et al. | 600/373 |
| 2011/0034912 | A1 * | 2/2011 | de Graff et al. | 606/21 |
| 2012/0046721 | A1 * | 2/2012 | Koop | 607/116 |
| 2012/0089205 | A1 * | 4/2012 | Boyden et al. | 607/88 |
| 2012/0136420 | A1 * | 5/2012 | Pardoel et al. | 607/116 |
| 2013/0018251 | A1 * | 1/2013 | Caprio et al. | 600/393 |

FOREIGN PATENT DOCUMENTS

| | | |
|---|---|---|
| WO | 2011057276 | 5/2011 |
| WO | 2011067297 | 6/2011 |

OTHER PUBLICATIONS

International Search, PCT/US2012/047994, Oct. 9, 2012.

* cited by examiner

Alignment jig

NEURAL DEVICE WITH MODULAR ELECTRODE ARRAY

CLAIM OF PRIORITY

This application claims the benefit of priority under 35 U.S.C. §119(e) of Kipke et al., U.S. Provisional Patent Application Ser. No. 61/511,343, filed Jul. 25, 2011, which is incorporated by reference herein in its entirety.

TECHNICAL FIELD

This invention relates generally to the neural devices field, and more specifically to an improved neural device with modular electrode array in the neurotechnology field.

BACKGROUND

Surface neural recording and stimulation involves placing an electrode array directly on the surface of the targeted neural tissue. The electrode array typically includes electrode sites that sense electrical activity in the tissue and can be used to assess neuronal activity. The electrode sites can also deliver small electrical currents to the tissue and can be used to stimulate neuronal activity. For example, electrocorticography, or ECoG, involves placing an electrode array directly on the cerebral cortex, the outer surface of the brain. ECoG can be used in epilepsy mapping procedures conducted to identify and locate diseased tissue in preparation for surgical resection of the diseased tissue. However, conventional surface arrays are large and have a limited spatial resolution that reduces the precision of sensed electrical activity or stimulated electrical activity, resulting in reduced precision of gathered neural activity information or activation. Thus, there is a need in the neural devices field to create an improved neural device with modular electrode arrays. This invention provides such an improved neural device.

DETAILED DESCRIPTION

The following description of example embodiments of the invention is not intended to limit the invention to these embodiments, but rather to enable any person skilled in the art to make and use this invention.

Figure 1:
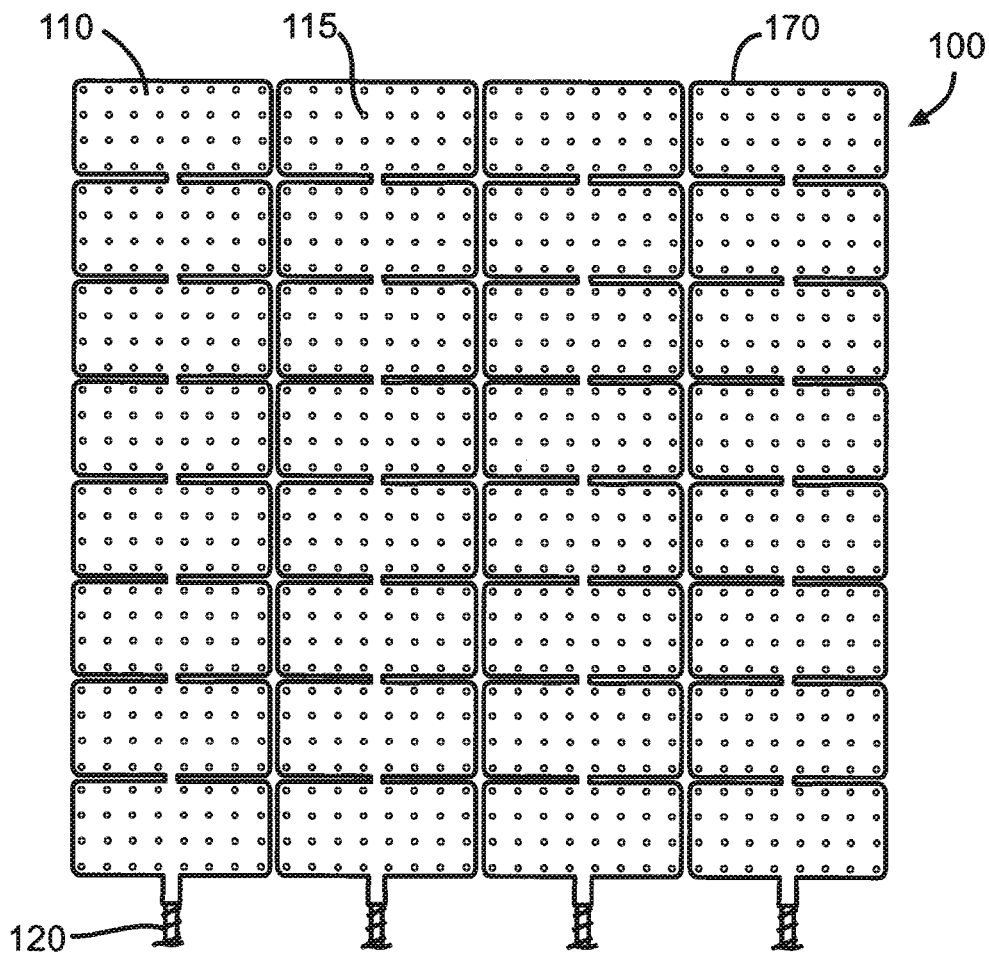
FIG. 1 is a schematic of an example of a neural device, consistent with some example embodiments of the invention.

FIG. 1 shows an example of a neural device 100. The neural device 100 includes modular electrode array. The modular electrode array includes a modular flexible substrate. The modular flexible substrate includes a plurality of electrode modules 110. An electrode module 110 can be planar and can include a plurality of electrodes 115. The electrodes 115 may be configured to sense a neural signal at a neural source or deliver neural stimulation energy to a neural target. As is described herein, multiple signals can be sensed by a group or subset of the electrodes to form a composite signal. The group of electrodes used in sensing the composite signal can be called a macroelectrode and the individual electrodes can be called microelectrodes. The electrodes 115 can be called microelectrodes because of their small size. The modular flexible substrate can include a spatial separation between the electrode modules 110. The modular electrode array also includes conductive interconnect 120 (e.g., conductive traces or wires) coupled to the plurality of microelectrodes. The conductive interconnect 120 may be used to one or both of route electrical signals sensed by the electrodes and route stimulus signals to the electrodes. The interconnect 120 can be used to carry signals between modules or to carry signals between the modular electrode array and a device separate from the neural device 100. The modular flexible substrate may be supported by a backing 170 of flexible material, such as silicone or another flexible polymer.

Figure 2:
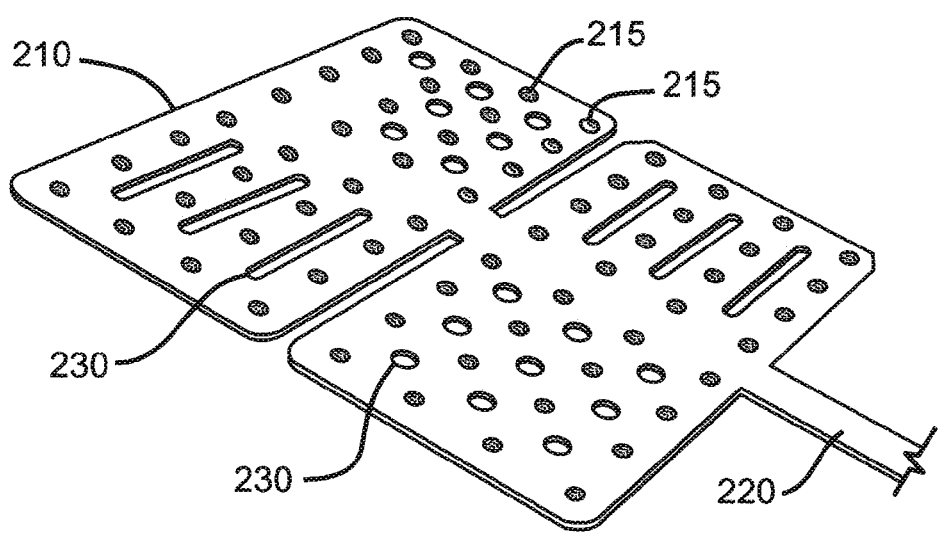
FIG. 2 is a detailed schematic of an example of an electrode module in the modular electrode array in a neural device, consistent with some example embodiments of the invention.

FIG. 2 shows an example of an electrode module 210 that is planar. The electrode module 210 can include an array of microelectrodes 215 and can include one or more apertures 230. The apertures 230 may have different shapes, such as slots or circles as shown in the example. In some variations, the electrode module 210 may be preformed to have a particular curvature in order to conform to known anatomy of the target tissue. The electrode module 210 can be a flexible thin-film microfabricated structure, such as a polymer substrate. The polymer substrate may be parylene or polyimide, but may additionally and/or alternatively include any suitable material. Layers of materials can be deposited on the substrate and patterned through microfabrication processes such as those used in manufacture of semiconductors. The flexible thin-film microfabricated structure may be supported by a backing of flexible material. However, the module may be made in any suitable manner. A conductive interconnect 220, similar to interconnect 110 in FIG. 1, is shown.

The microelectrodes 215 can be arranged in a microelectrode array of an approximately rectangular grid, although the microelectrodes 215 may include any number of microelectrodes 215 arranged in any suitable regular or irregular pattern. The microelectrode array can include recording electrodes that each provide a neural signal in a respective input channel, but additionally and/or alternatively may include stimulation or other kind of electrodes. In certain variations the microelectrodes 215 can be elliptical. In certain variations, the microelectrodes 215 can be approximately circular, but the microelectrodes 215 may be any suitable shape. In some examples, the electrode module 210 includes an array of microelectrodes that are substantially identical in size and shape. In some examples, the electrode module 210 includes an array of microelectrodes that differ in one or both of shape and size. In an illustrative non-limiting example, an electrode module 210 includes two substantially similar halves connected to each other. Each half including 32 microelectrodes (arranged in a 4×8 grid), such that each electrode module includes a total of 64 microelectrodes (arranged in an 8×8 grid) providing 64 channels of signal. The connected halves can be supported by a 1 mm thick silicone backing.

The apertures 230 of the electrode module 210 may allow passage of a penetrating electrode (e.g. elongated electrode shank) to be placed within the tissue. In some examples, one or more penetrating electrodes are included in the flexible substrate. In some examples, a penetrating electrode includes a microelectrode array attached to a carrier, such as an insulated wire. The apertures 230 may allow release of brain fluid or other fluid from the tissue, and/or increase mechanical flexibility of the module. As shown in FIG. 2, the apertures 230 may be elliptical holes (e.g. circular apertures to permit defined placement of cylindrical penetrating electrodes), slots, or any suitable shape, such as a custom shape configured to permit passage of a particular instrument through the module. The neural device may include one or more waveguides (e.g., an optical fiber) that delivers light to at least a portion of the one or more apertures. In some variations, the apertures may form a series of ribs that increase the flexibility of a particular portion of the module. The apertures 230 may be interspersed between the microelectrodes 215 in a regular pattern. Alternatively, the electrode module 210 may not define any apertures and/or separate halves or other portions.

Multiple electrode modules can be combined to form the modular electrode array. The electrode modules may be combined to form a rectangular grid. The resulting rectangular grid can include microelectrodes that are distributed in a regular fashion within the rectangular grid. For example, as shown in FIG. 1, the modular electrode array includes 16 electrode modules arranged in four columns of four modules each. Each electrode module shown includes two connected portions including a total of 64 microelectrodes, such that the modular electrode array includes 1024 microelectrodes arranged in a regular 32×32 grid and providing 1024 channels of signal. In an alternative arrangement providing a similar layout of 1024 microelectrodes, the modular electrode array may include 32 modules arranged in an 8×4 grid, where each module includes 32 microelectrodes.

Figure 3A:
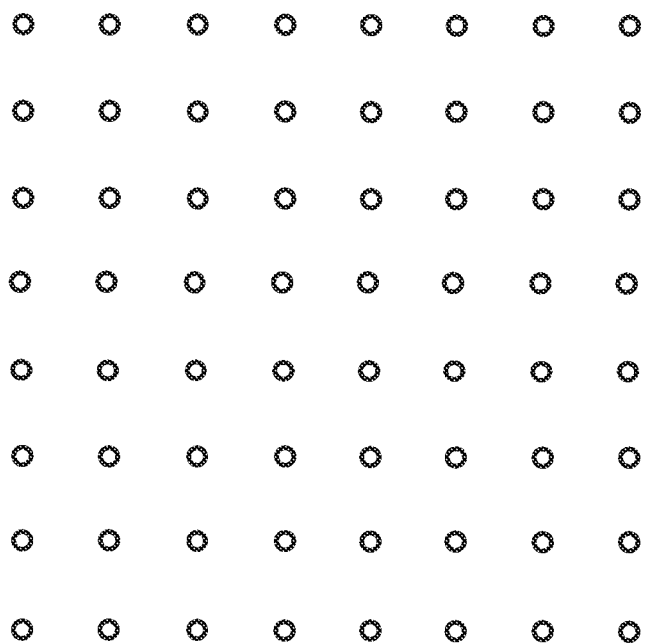
FIGS. 3A and 3B show a comparison of the microelectrode distribution between a conventional ECoG device and an example of a neural device consistent with some example embodiments of the invention, respectively.
Figure 3B:
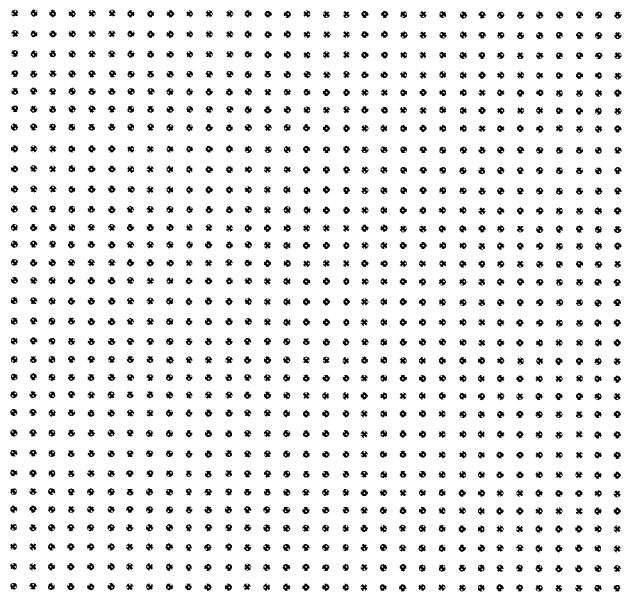

FIGS. 3A and 3B illustrate a comparison of conventional electrode spacing (FIG. 3A) and spacing using microelectrodes (FIG. 3B). The spacing shown is for illustration purposes and is not meant to represent actual spacing of an actual device. In a non-limiting example, the diameter of a microelectrode can be 0.575 millimeters (mm) and pitch between microelectrodes can be 2.5 mm. The microelectrodes and the corresponding conductive traces coupled to the microelectrodes can be fabricated using microfabrication techniques to achieve the required spacing. Comparison of the FIGURES shows that an ECoG device having an array of 1024 microelectrodes takes up substantially the same area as an array of 64 conventional electrodes. Thus, an ECoG device having an array of microelectrodes includes more electrodes and conductive channels than a conventional 64-channel ECoG device.

Figure 4:
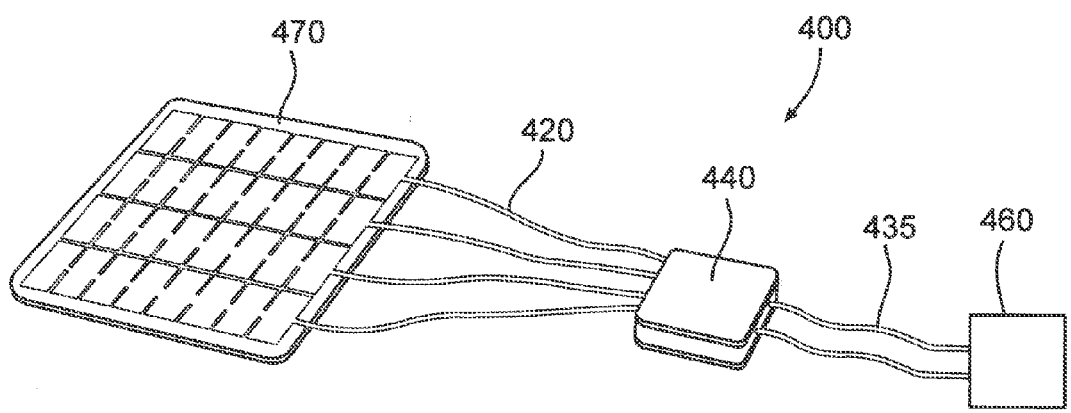
FIG. 4 is a schematic of an example of a neural device, consistent with some example embodiments of the invention.

FIG. 4 shows an example of a system 400 that includes a neural device. The neural device includes a modular electrode array. The modular electrode array includes a modular flexible substrate that includes a plurality of electrode modules with a spatial separation between the electrode modules. A flexible backing 470 may support the modular flexible substrate. The electrode modules include electrodes and the modular electrode array includes conductive interconnect coupled to the electrodes. The system 400 also includes a plurality of electrically conductive leads 435 and an electronic subsystem 440 coupled to the electrically conductive leads 435 and the conductive interconnect of the modular electrode array. In some examples, the conductive interconnect includes conductive traces 420 arranged to extend between the modular electrode array and the electronic subsystem 440. In some examples, the number of electrical leads is less than the number of conductive traces. The electronic subsystem can include a multiplexer circuit to selectively transfer signals sensed by a subset of the plurality of conductive traces to one or more of the electrically conductive leads.

Figure 5:
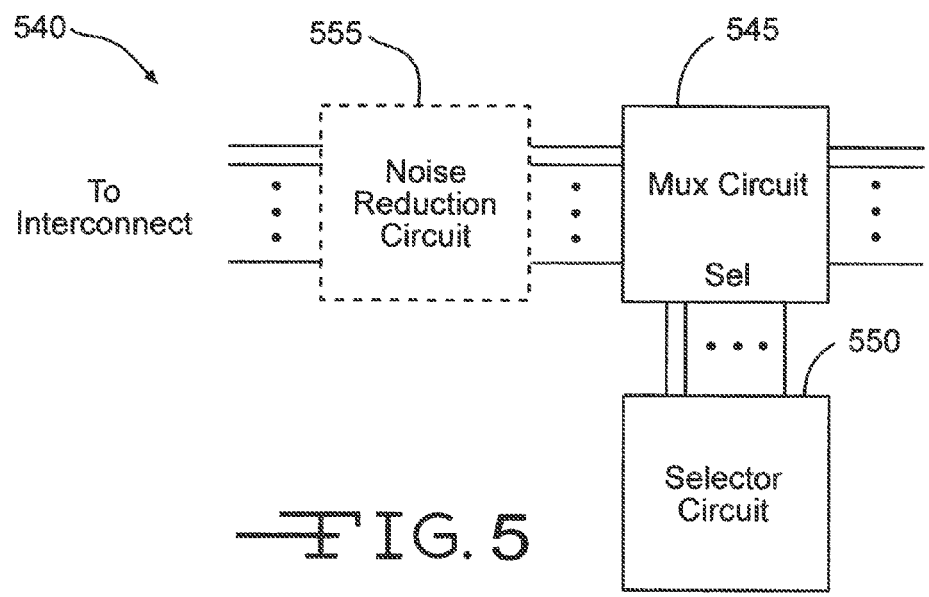
FIG. 5 shows a block diagram of portions of an example of an electronic subsystem.

FIG. 5 shows a block diagram of an example of an electronic subsystem 540. The electronic subsystem 540 includes a multiplexer circuit 545 having signal inputs, select inputs, and one or more signal outputs. The signal inputs to the multiplexer circuit 545 can be electrically coupled to the conductive channels of the flexible substrate shown in FIG. 4. The electronic subsystem 540 also includes a selector circuit 550 electrically coupled to the select inputs of the multiplexer circuit and configured to activate the select inputs to direct a signal from an input of the multiplexer circuit to an output of the multiplexer circuit 545. In some variations, the electronic subsystem can include a noise reduction circuit 555 (e.g., one or more filter circuits) to reduce signal noise.

Returning to FIG. 4, the system 400 can include a recording system 460 electrically coupled to the plurality of electrically conductive leads. In certain examples, the recording system 460 includes a data acquisition system (DAQ) that can include one or more of an analog to digital converter (ADC), a processor, and a memory. Multiplexing by the electronic subsystem 440 can reduce the number of recording channels needed in the recording system. Reducing the number of channels may enable the modular electrode array to be operable with a standard interface (e.g., conventional medical lead technologies having discrete wires). However, the electronic subsystem may interface with custom or other suitable lead systems. In some variations, the electronic subsystem may lack a multiplexer such that the number of conductive traces (input channels) is equal to the number of leads coupled to the recording system, and/or may include other suitable front-end electronics, such as signal processing or noise reduction. Alternatively, the neural device may lack an electronic subsystem, such that the conductive traces also function as leads that directly couple the modular electrode array to the recording system. In this alternative, the conductive traces may be coupled to more durable leads more suitable for use external to the body, such as a ribbon cable.

The modular electrode array of the neural device can include recording microelectrodes on the electrode modules that may be operable individually to record respective neural signals, and/or may be grouped in patterns of different sizes and/or shapes to emulate functionality of a macroelectrode. The neural device is selectively capable of sensing signals along a gradient of precision such that the user (e.g. neurologist) can "zoom" in on a particular area of tissue and sense from any number of the microelectrodes in a more precise manner, thereby gathering more detailed and "richer" information about the tissue. The neural device is also selectively capable of providing stimulation currents focused along a gradient of precision. The neural device can be used for electrocorticography (ECoG), such as in mapping brain tissue in an epileptic patient to more accurately and precisely identify and locate diseased tissue for surgical resection, or mapping cortical functions. In some embodiments, the neural device can be used for coverage of stimulation and/or recording of other tissue surfaces, such as those of the spinal cord, peripheral nerve, and/or muscle. However, the neural device may be used for any suitable neural recording and/or stimulation applications. In certain variations, the neural device uses the electrodes for impedance measurements, such as by using a first set of electrodes for applying a known current and a second set of electrodes to measure the voltage resulting from the applied current. Ohm's Law can then be used to determine the impedance of the tissue.

Figures 6A, 6B:
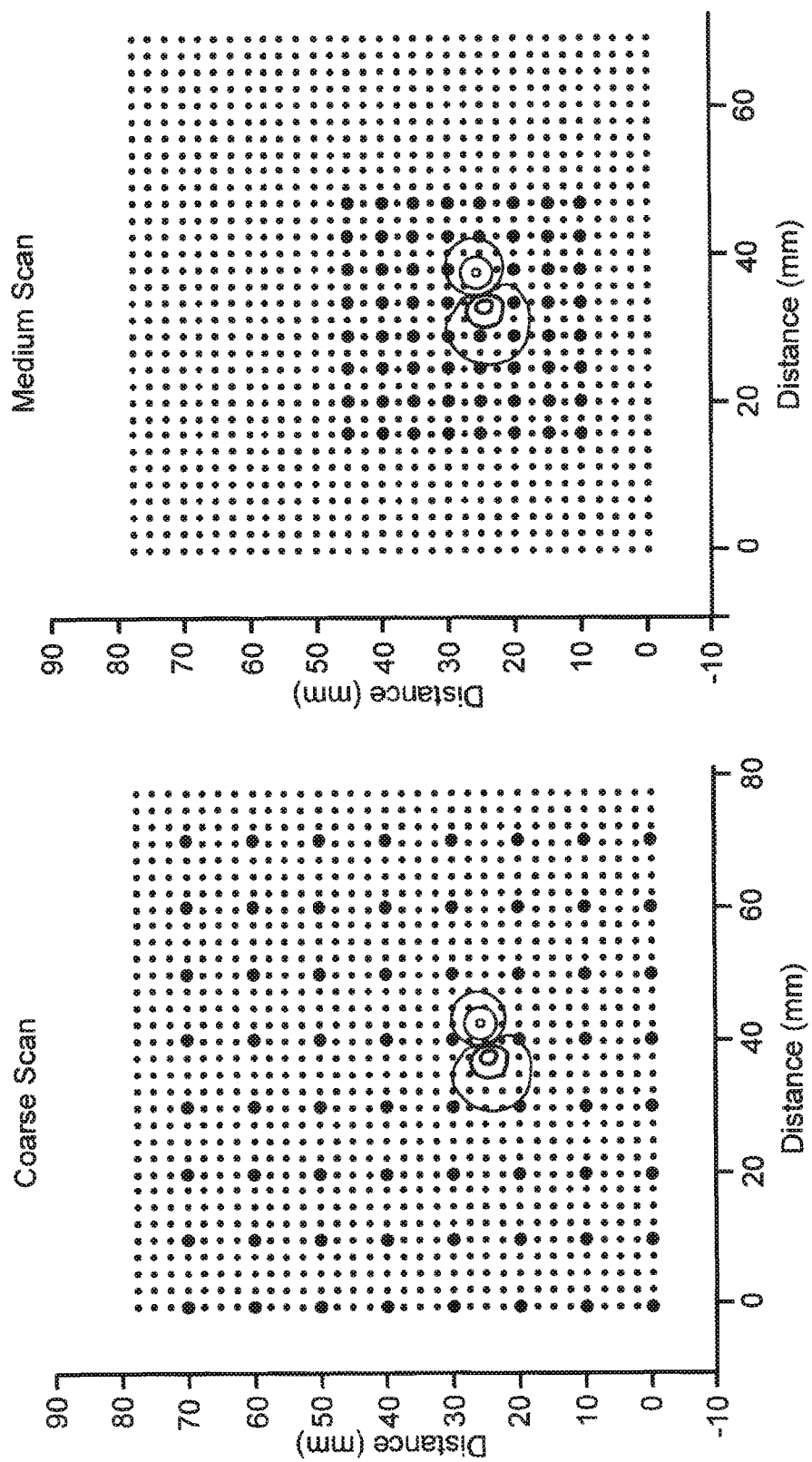
FIGS. 6A-6C is an illustration of an example of multi-scale functionality of a neural device consistent with some example embodiments of the invention.
Figure 6C:
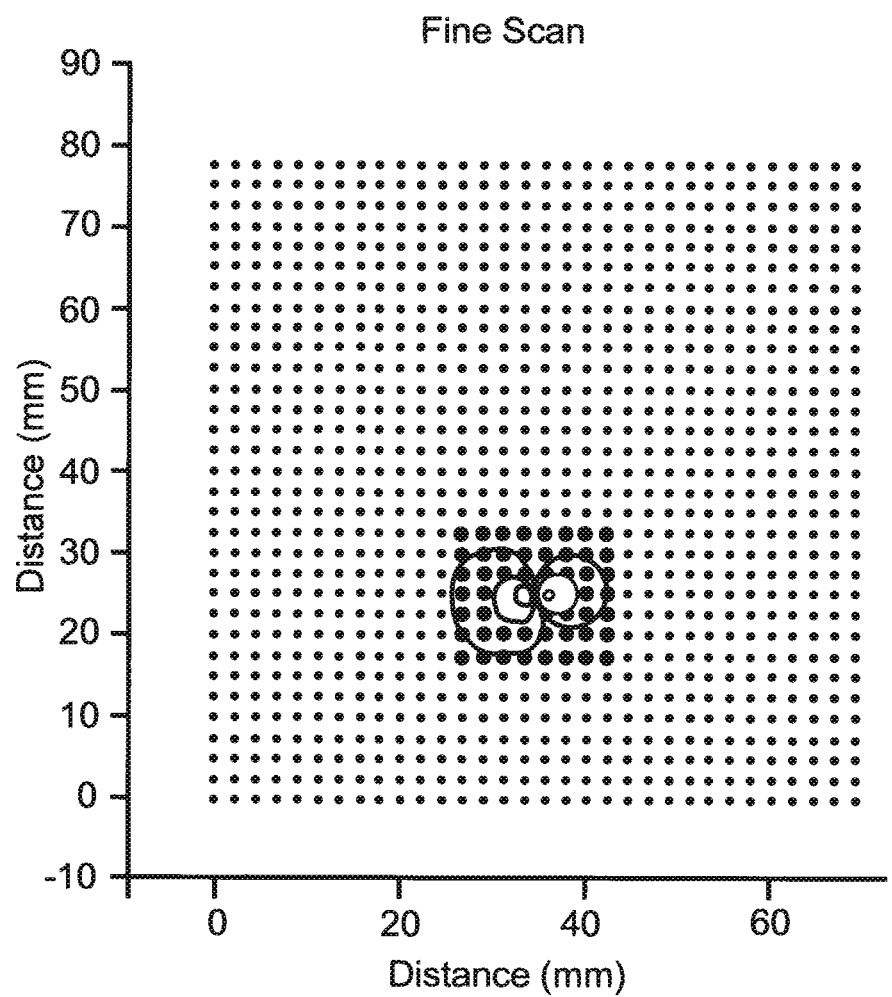

The recording microelectrodes on the electrode modules may be operable individually to record respective neural signals, and/or may be grouped in patterns of different sizes and/or shapes to emulate functionality of a macroelectrode. A macroelectrode can be used to produce a composite signal that may be more appropriate for the desired analysis. Additionally, a composite signal can be interpreted as a signal from a conventional probe (e.g., a probe with a comparatively large electrode) allowing a user to perform similar analysis appropriate for conventional ECoG. A macroelectrode can also be used to stimulate a larger volume of tissue. Furthermore, the neural device can be selectively capable of sensing signals along a gradient of precision such that the user (e.g. a neurologist) can "zoom" in on a particular area of tissue and sense signals from any number of the microelectrodes in a more precise manner, thereby gathering more detailed and "richer" information about the tissue. The microelectrodes may be operated to scan in varying levels of resolution, such as by operation of the electronic subsystem 440 in FIG. 4. For instance, as shown in FIG. 6A, in a coarse scan only a portion of the microelectrodes, loosely distributed across the tissue surface, are activated in a lower "resolution" of signal capture. In the coarse scan mode, a rough area of interest (e.g. dipole surface projection) may be identified and then given closer inspection in a medium scan (FIG. 6B) in which a more tightly distributed portion of the microelectrodes around the area of interest are activated. The area of interest may be even more closely analyzed in a fine scan mode (FIG. 6C) that may activate all or nearly all of the nearby microelectrodes around that area. The resolution level of a scan may lie along any point in a gradient of resolution.

In some embodiments, at least a portion of the electrode modules may be specifically designed for particular functions and/or fits of targeted tissues. For instance, the thickness, footprint area shape, degree of flexibility, distribution or layout of microelectrodes, other module surface characteristics such as bioactive coatings, and/or any suitable characteristic of the module may be customized or specifically designed for a particular region or type of tissue, such as to conform closely with brain surfaces of gyrated brain (e.g. hugging crown of gyms, following sulcus). In other words, this customizability of the modular electrode array also enables the neural device to be highly conformal and of a specialized design to conform to particular surface features.

Figure 7A:
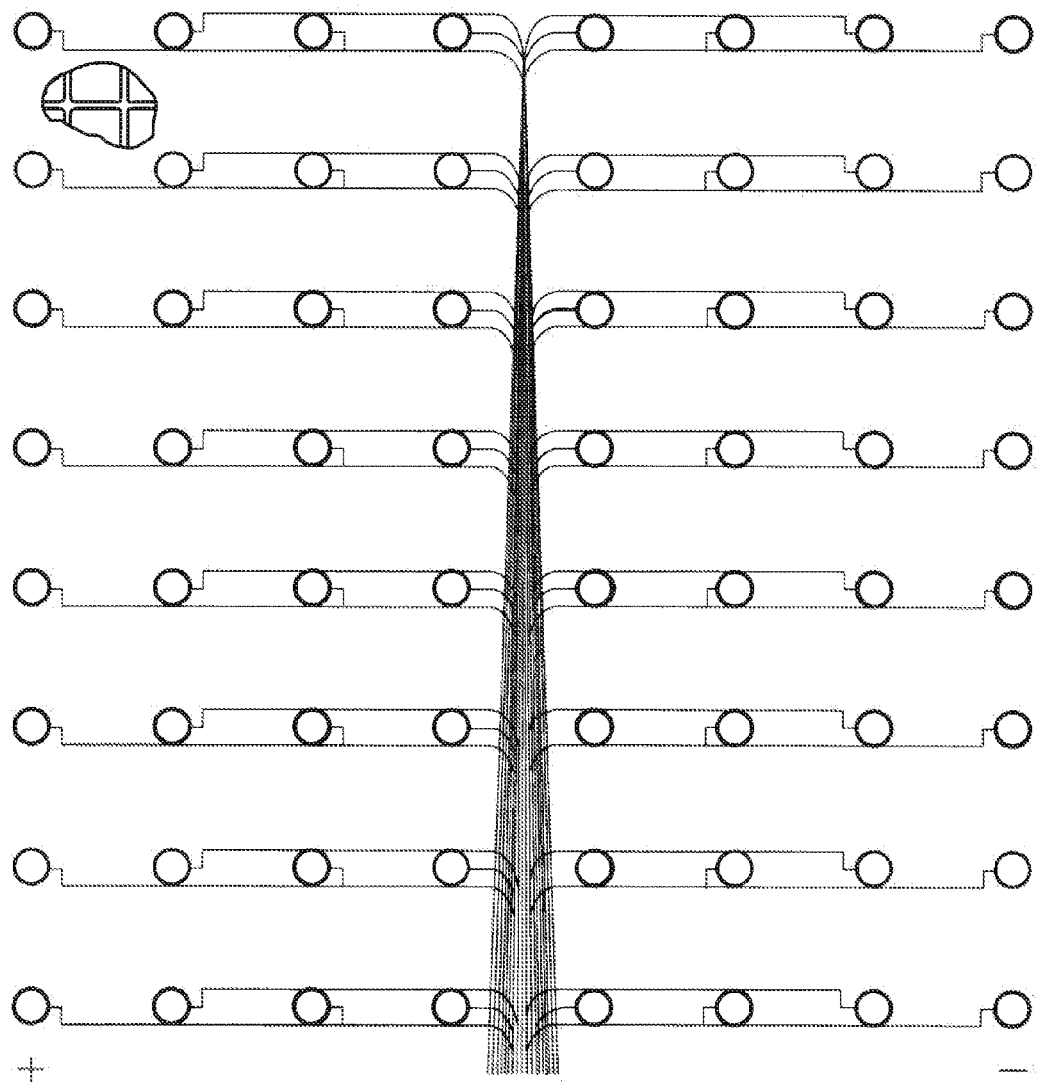
FIGS. 7A and 7B show detailed schematics of examples of interconnects in a neural device of a preferred embodiment.
Figure 7B:
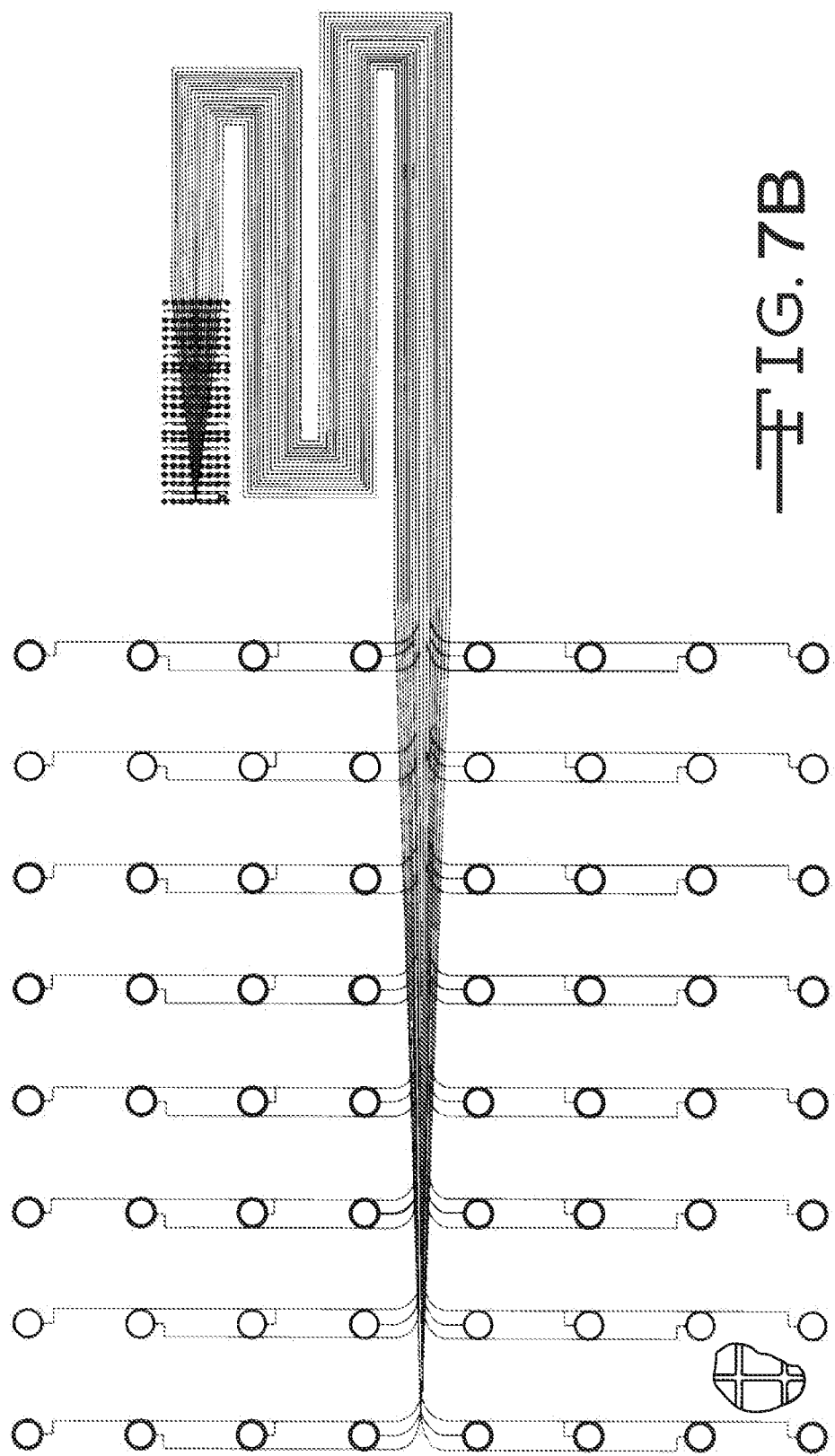

The interconnect functions to transfer signals to and from the modular electrode array. The interconnect can include conductive traces coupled to a respective module, and (as shown in FIG. 7A) conductive traces can be individually coupled to a microelectrode of the electrode module. The conductive traces may branch bilaterally symmetrically from the centerline of the electrode module. As shown in FIG. 7B, relative to each electrode module, conductive traces can be arranged in a serpentine pattern, but may alternatively be arranged in any suitable manner. The flexible substrate may include a thin-film electrical signal filter (e.g., a low pass filter) microfabricated and conductively coupled to one or more of the conductive traces.

Figure 8:
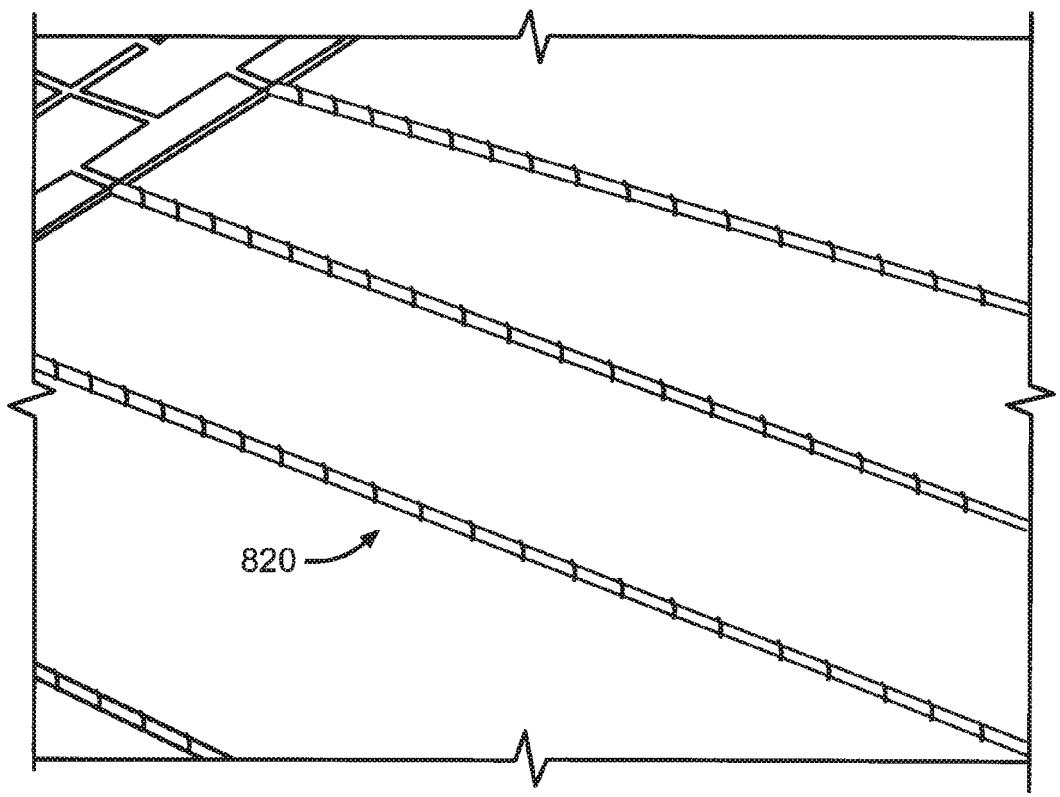
FIG. 8 is a schematic of an example of coiled interconnects in a neural device, consistent with some example embodiments of the invention.

FIG. 8 shows an example of interconnect for a neural device. The interconnect can include conductive traces 820 that can be gathered and helically coiled in groups, although the conductive traces 820 may alternatively be ungrouped and/or uncoiled. The spiral shape of the conductive traces 820 may reduce the electrical currents that are induced during magnetic resonance imaging (MRI), thereby making the neural device safe for use with MRI procedures that are often used to help place ECoG and other neural devices on target tissue. The coiled traces may be insulated with a flexible material (e.g., silicone). The conductive traces 820 may be coiled around a tube of flexible material. The interconnect may also include waveguides (e.g. thin-film waveguides, optical fibers) for guided light transmission in the device that can be used for optical stimulation or optical sensing of the tissue in the vicinity of the device.

Figure 9:
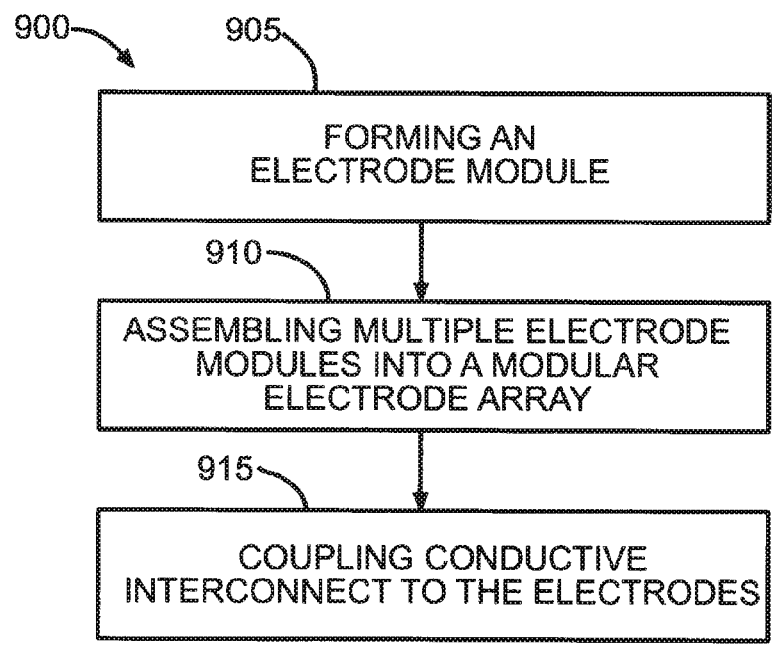
FIG. 9 shows a flow diagram of an example of method of manufacturing a neural device.

FIG. 9 shows a flow diagram of an example of method 900 of manufacturing a neural device. Manufacturing the neural device includes manufacturing the modular electrode array and manufacturing the interconnect. At block 905, electrode modules are formed. An electrode module includes a plurality of electrodes disposed on a planar module. The electrodes can be microelectrodes. One or more apertures can be formed in one or more of the electrode modules. The electrode modules may be manufactured using thin film microfabrication techniques.

Figure 10A:
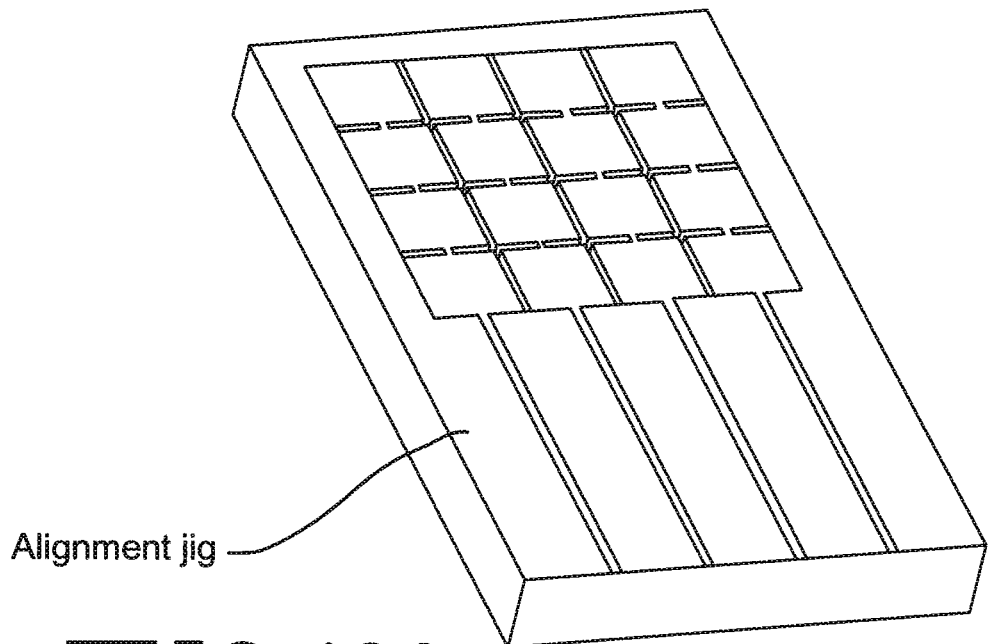
FIGS. 10A-D and 11A-C illustrate an example of a method of manufacturing and assembling a neural device, consistent with some example embodiments of the invention.
Figure 10B:
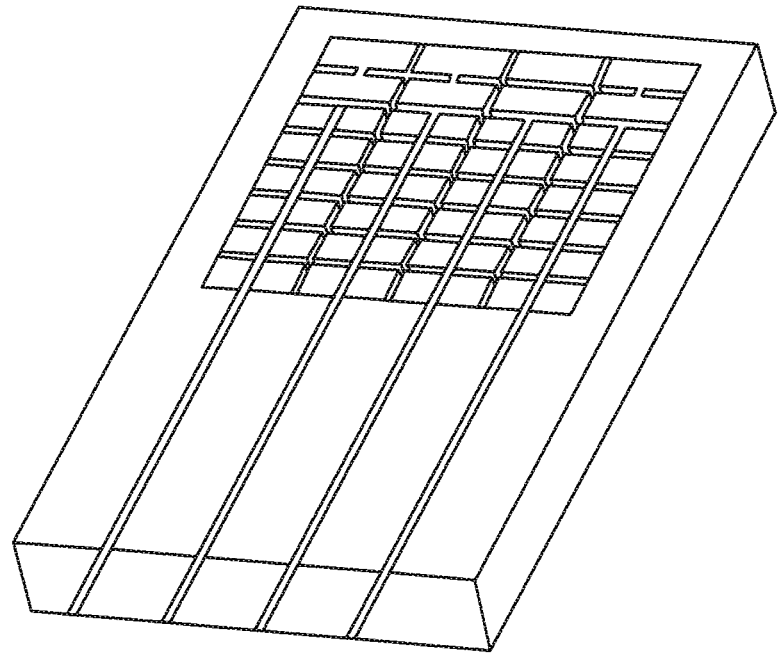

At block 910, multiple electrode modules are assembled into a modular electrode array. The individual electrode modules may include electrodes disposed on a planar flexible substrate and assembling the electrode modules may form a modular flexible substrate that includes the plurality of electrode modules and a spatial separation between adjoining electrode modules to form the modular electrode array. Manufacture of the neural device can include alignment and/or predictable relative positioning of the electrode modules in the modular electrode array. As shown in FIGS. 10A and 10B, manufacturing the modular electrode array can include laying the plurality of modules in an alignment jig, adhering the plurality of modules to one another, and injection molding a backing to the adhered modules. The jig can defines recesses, each receiving a respective module, and networked channels that join two or more recesses together. The jig can include a 4×4 rectangular grid for 16 modules, but may alternatively have any suitable number of recesses in other arrangements. For the general case, the modular electrode array can include X rows of electrode modules and Y columns of electrode modules to an X by Y electrode array; where X and Y are positive integers. In laying the modules in respective recesses, the respective interconnects can be gathered at one end and stacked in groups. Adhering the plurality of modules to one another can include applying epoxy to adjoining surfaces of the modules. The epoxy can be a UV-curable epoxy, but may be any suitable kind of adhesive. Alternatively, the modules may be joined with other coupling processes or mechanisms such as heat welding or with fasteners.

Figure 10C:
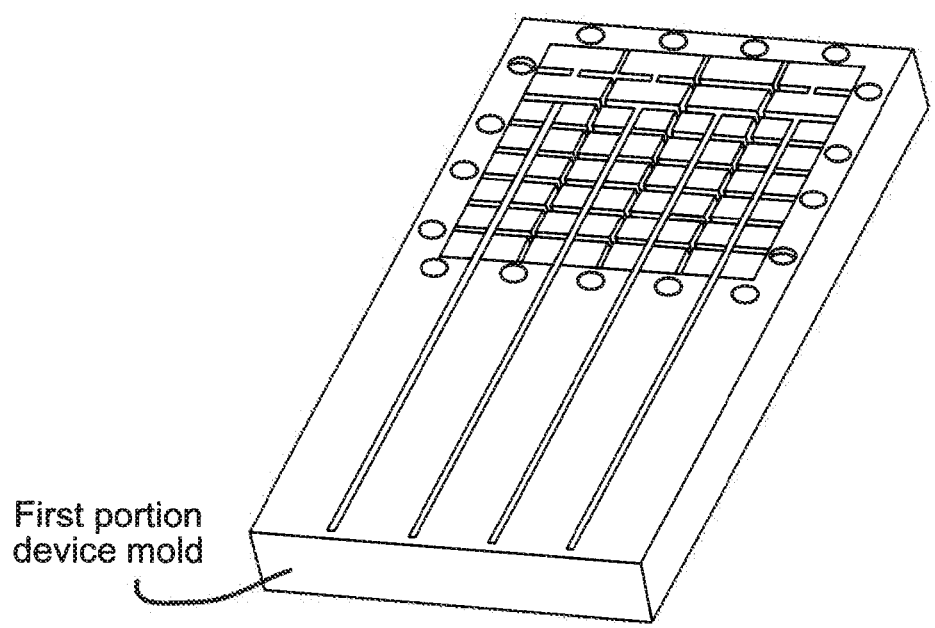
Figure 10D:
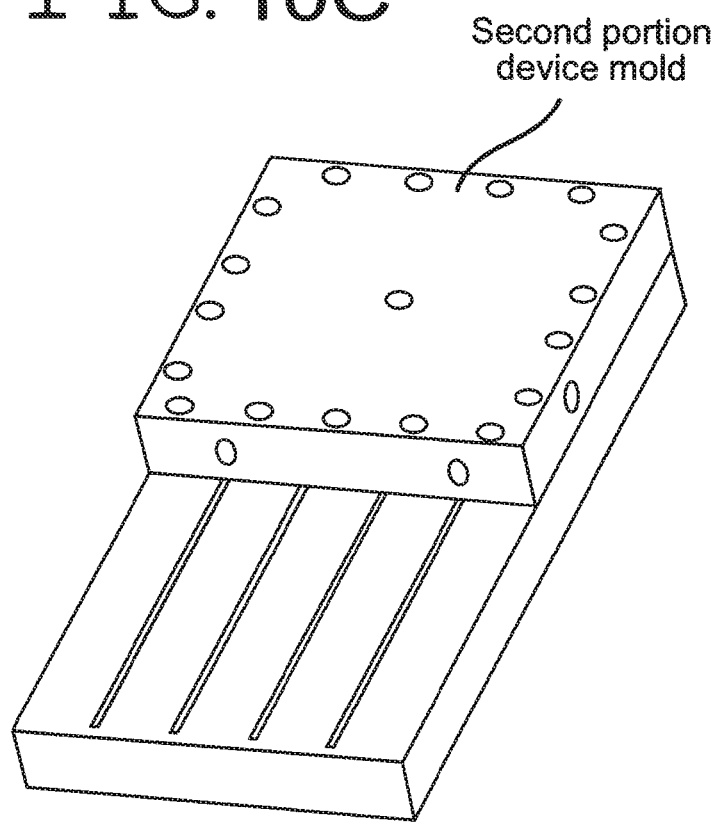

The process can include attaching a backing to the modular flexible substrate. The backing can be attached by injection molding or adhering the backing to the modular flexible substrate. Injection molding a backing to the adhered modules can include placing the adhered modules in a device mold, injecting backing material into the device mold, curing the backing material, and releasing modular electrode array from the device mold. As shown in FIGS. 10C and 10D, the adhered modules can be placed in a first portion (e.g. bottom half) device mold and a second portion (e.g. top half) device mold can be aligned to the first portion device mold with pegs. After the first and second portion molds are clamped together, the backing material (e.g. silicone) can be injected into the device mold and cured in an oven, thereby simultaneously forming the backing shape and adhering the backing material to the coupled modules. After curing, the device mold is opened and the backed modular electrode array is released. Other variations of the injection molding process may be used, such as those known and used by one ordinarily skilled in the art.

Figure 11A:
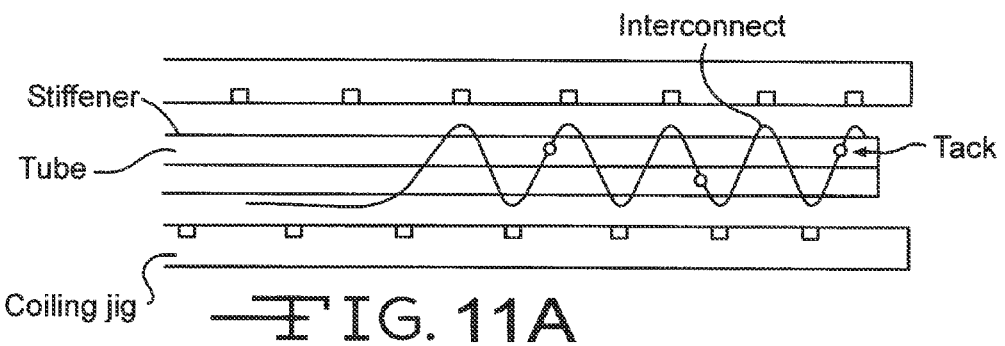

Returning to FIG. 9, conductive interconnect is formed and coupled to the electrodes at 915. The conductive interconnect can include conductive traces arranged in a serpentine pattern. The conductive traces can be separated and folded into a different arrangement (e.g., substantially straight). Interconnect can also be formed by grouping the conductive traces and helically coiling the grouped traces. Insulation can be injection molded around the coiled interconnect. At least a portion of the neural device may remain in the device mold during these steps. As shown in FIG. 11A, a group of conductive channels helically coiled or wrapped around a tube can be placed in a coiling jig that regulates the spacing and/or tension of the coiling. During coiling, portions of the traces may be periodically tacked to the tube (e.g., with cyanoacrylate adhesive) to prevent uncoiling. The tube can be made of a flexible material such as silicone, and may include a stiffener such as a metal wire inserted in a lumen of the tube, to increase rigidity of the tube during coiling of the lead. The stiffener may or may not be removed from the tube after coiling. In some examples, each group of conductive channels is preferably coiled separately. For instance, four different groups of traces may be coiled around four different tubes.

Figure 11B:
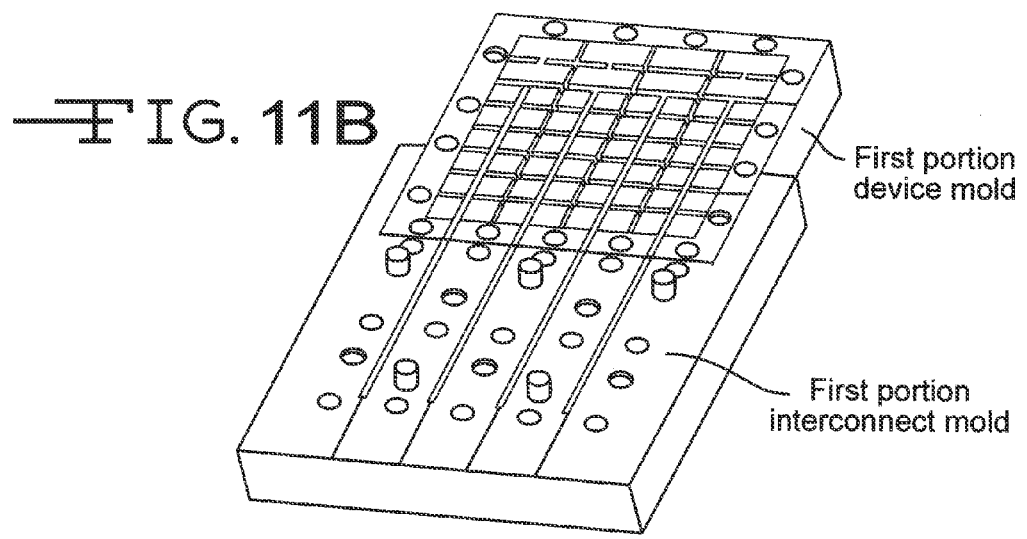
Figure 11C:
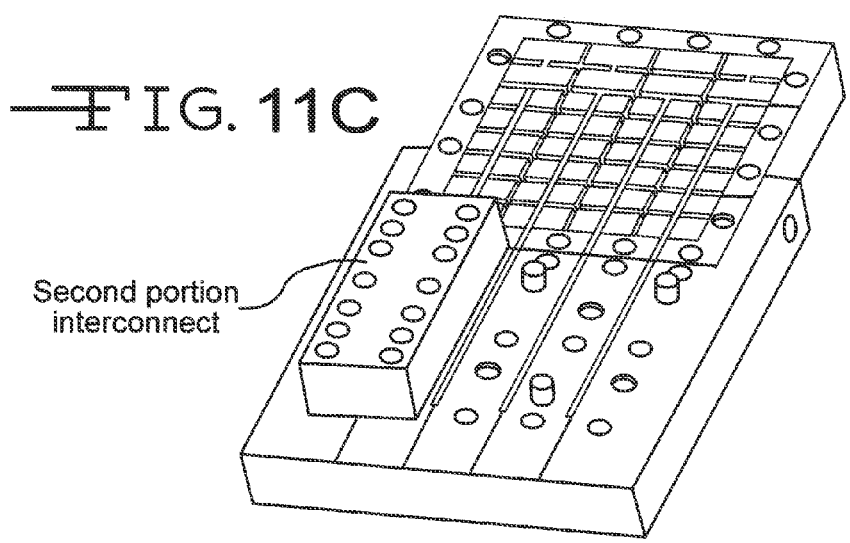

Injection molding the insulation around the coiled conductive traces can be similar to the step of injection molding the backing of the modular electrode array and/or other injection molding processes. As shown in FIGS. 11B and 11C, the coiled traces are preferably placed in a first portion (e.g. bottom half) interconnect mold and a second portion (e.g. top half) is aligned to the first portion interconnect mold with pegs. After the first and second portion interconnect molds are clamped together, the insulation material (e.g. silicone) is injected into the interconnect mold and cured in an oven, thereby simultaneously forming the insulation shape and adhering the insulation around the coiled interconnects. Each group of the coiled traces can be individually overmolded with insulation at separate times, although alternatively the coiled traces may simultaneously be overmolded with insulation.

In some embodiments, some portions of the device molds, coiling jig, and/or interconnect molds may be reused it multiple steps. For instance, a portion of the bottom half device mold may be adapted to clamp to (1) the upper half device mold when injecting molding the backing of the modular electrode array, (2) the coiling jig when coiling the interconnects and (3) a portion of the bottom half interconnect mold when injection molding the insulation around the coiled interconnects. However, the device may alternatively be placed in separate molds and/or jigs for each step of the process.

Additional Notes and Examples

Example 1 includes subject matter such as apparatus comprising a modular electrode array including a modular flexible substrate. The modular flexible substrate includes a plurality of electrode modules. An electrode module includes a plurality of electrodes disposed on a planar module. The flexible substrate also includes a spatial separation between the electrode modules, and the modular electrode array includes conductive interconnect coupled to the electrodes of the plurality of electrodes.

In Example 2, the subject matter of Example 1 optionally includes a multiplexer circuit and a selector circuit. The multiplexer circuit includes signal inputs, select inputs, and one or more signal outputs, wherein the signal inputs to the multiplexer circuit are electrically coupled to the conductive interconnect. The selector circuit is electrically coupled to the select inputs of the multiplexer circuit and configured to activate the select inputs to direct a signal from an input of the multiplexer circuit to an output of the multiplexer circuit.

In Example 3, the subject matter of one or any combination of Examples 1 and 2 optionally includes conductive interconnect that includes conductive traces arranged in a serpentine pattern.

In Example 4, the subject matter of one or any combination of Examples 1 and 2 optionally includes conductive interconnect that includes groups of conductive traces helically coiled.

In Example 5, the subject matter of Example 4 optionally includes groups of conductive traces helically coiled around a tube containing flexible material.

In Example 6, the subject matter of one or any combination of Examples 1-5 optionally includes a flexible substrate that includes a flexible thin-film substrate.

In Example 7, the subject matter of one or any combination of Examples 1-6 optionally includes a modular flexible substrate that includes one or more thin film electrical signal filters conductively coupled to the conductive interconnect.

In Example 8, the subject matter of one or any combination of Examples 1-7 optionally includes one or more electrode modules having one or more apertures.

In Example 9, the subject matter of Example 8 optionally includes at least one wave guide configured to deliver light to at least a portion of the one or more apertures.

In Example 10, the subject matter of one or any combination of Examples 1-9 optionally includes a modular flexible substrate that includes one or more penetrating electrodes.

In Example 11, the subject matter of one or any combination of Examples 1-10 optionally includes a plurality of electrodes configured to both receive a neural signal from a neural signal source and provide electrical stimulation energy to a neural stimulation target.

Example 12 can include subject matter (such as a method, a means for performing acts, or a machine-readable medium including instructions that, when performed by the machine, cause the machine to perform acts), or can optionally be combined with the subject matter of one or any combination of Examples 1-11 to include subject matter comprising disposing a plurality of electrodes on a plurality of planar modules to form a plurality of electrode modules, forming a modular substrate, and coupling conductive interconnect to the plurality of electrodes. The modular flexible substrate includes the plurality of electrode modules and a spatial separation between adjoining electrode modules to form a modular electrode array.

In Example 13, the subject matter of Example 12 optionally includes forming a plurality of flexible electrode modules, and adhering the flexible electrode modules to one another to form the modular flexible substrate.

In Example 14, the subject matter of one or any combination of Examples 12 and 13 optionally includes forming a plurality of X times Y electrode modules, and adhering the modules to form an X by Y electrode module array, wherein X and Y are positive integers.

In Example 15, the subject matter of Example 14 optionally includes X=Y.

In Example 16, the subject matter of one or any combination of Examples 12-15 optionally includes attaching a backing to the modular flexible substrate.

In Example 17, the subject matter of Example 16 optionally includes injection molding a silicone backing and attaching the modular flexible substrate to the silicone backing.

In Example 18, the subject matter of Example 16 optionally includes adhering a thin-film backing to the modular flexible substrate.

In Example 19, the subject matter of one or any combination of Examples 12-18 optionally includes forming one or more conductive traces arranged in a serpentine pattern.

In Example 20, the subject matter of one or any combination of Examples 12-18 optionally includes helically coiling one or more groups of conductive traces.

In Example 21, the subject matter of Example 20 optionally includes helically coiling the groups of conductive traces around a tube containing flexible material.

In Example 22, the subject matter of one or any combination of Examples 12-21 optionally includes forming one or more apertures in one or more of the electrode modules.

Example 23 includes subject matter (such as a system), or can optionally be combined with the subject matter of one or any combination of Examples 1-22 to include such subject matter, comprising a plurality of electrically conductive leads and a modular electrode array. The modular electrode array includes a modular flexible substrate that includes a plurality of electrode modules, a spatial separation between the electrode modules, and conductive interconnect coupled to the electrodes of the plurality of electrodes. An electrode module includes a plurality of electrodes disposed on a planar module. The subject matter also includes an electronic subsystem electrically coupled to the conductive interconnect and the electrically conductive leads. The electronic subsystem is configured to transfer sensed electrical signals from the conductive interconnect to the plurality of electrically conductive leads.

In Example 24, the subject matter of Example 23 optionally includes conductive interconnect having a plurality of conductive traces. The number of electrically conductive leads is less than the number of conductive traces, and the electronic subsystem includes a multiplexer circuit configured to selectively transfer signals sensed by a subset of the plurality of conductive traces to one or more of the electrically conductive leads.

In Example 25, the subject matter of one or any combination of Examples 23 and 24 optionally includes a noise reduction circuit.

In Example 26, the subject matter of one or any combination of Examples 23-25 optionally includes a recording system electrically coupled to the plurality of electrically conductive leads.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A modular electrode array, comprising:
 a) a first electrode module, comprising:
  i) a first flexible substrate comprising a first perimeter; and
  ii) at least two first electrodes supported on a first side of the first substrate,
  iii) wherein the at least two first electrodes are spaced apart from each other by a first pitch length of the first substrate;
 b) a second electrode module, comprising:
  i) a second flexible substrate comprising a second perimeter; and
  ii) at least two second electrodes supported on a first side of the second substrate, iii) wherein the at least two second electrodes are spaced apart from each other by a second pitch length of the second substrate;

c) a first connector substrate extending along a first longitudinal axis from a first connector end to a second connector end, wherein:
   i) the first connector end is connected to the first substrate perimeter and the second connector end is connected to the second substrate perimeter to thereby provide a spatial separation between the first and second modules, and
   ii) wherein the first longitudinal axis of the first connector substrate intersects both the first pitch between and spaced from the two first electrodes and the second pitch between and spaced from the two second electrodes; and d) at least two first conductive interconnects and at least two second conductive interconnects, each of the first and second conductive interconnects extending from a proximal interconnect end to a distal interconnect portion having a distal interconnect end,
   i) wherein the proximal first and second interconnect ends are configured for electrical connection to an external electrical device, and
   ii) wherein the distal portions of the first conductive interconnects are supported by the first flexible substrate with the first distal interconnect ends electrically coupled to respective ones of the at least two first electrodes, and
   iii) wherein the distal portions of the second conductive interconnects are supported by the first flexible substrate, the first connector substrate, and the second flexible substrate with the second distal interconnect ends electrically coupled to respective ones of the at least two second electrodes; and e) a backing supporting the first and second substrates and the intermediate first connector substrate on respective second sides thereof opposite the first sides to thereby maintain the spatial separation between the first and second modules.

2. The modular electrode array of claim 1, including:
a) a multiplexer circuit having signal inputs, select inputs, and one or more signal outputs, wherein the signal inputs to the multiplexer circuit are electrically coupled to the at least two first and second conductive interconnects; and
b) a selector circuit electrically coupled to the select inputs of the multiplexer circuit and configured to activate the select inputs to direct a signal from an input of the multiplexer circuit received from at least one of the at least two first and second electrodes electrically coupled to the respective at least two first and second conductive interconnects to an output of the multiplexer circuit.

3. The modular electrode array of claim 1, wherein at least one of the at least two first and second conductive interconnects comprises a conductive trace arranged in a serpentine pattern.

4. The modular electrode array claim 1, wherein there are a plurality of first and second conductive interconnects electrically connected to respective ones of a plurality of first and second electrodes and wherein the plurality of conductive interconnects include at least one group of helically coiled conductive traces.

5. The modular electrode array of claim 4, wherein the at least one group of conductive traces are helically coiled around a tube comprising flexible material.

6. The modular electrode array of claim 1, wherein at least one of the first and second flexible substrates comprises a flexible thin-film substrate.

7. The modular electrode array of claim 1, further comprising at least one electrical signal filter electrically coupled to at least one of the at least two first and second conductive interconnects.

8. The modular electrode array of claim 1, wherein at least one of the first and second electrode modules comprises at least one aperture through the respective first and second flexible substrate.

9. The modular electrode array of claim 8, including a wave guide configured to deliver light to the at least one aperture through the respective first and second flexible substrate.

10. The modular electrode array of claim 1, wherein at least one of the at least two first and second electrodes is a penetrating electrode.

11. The modular electrode array of claim 1, wherein at least one of the at least two first and second electrodes is configured to both receive a neural signal from a neural signal source and provide electrical stimulation energy to a neural stimulation target.

12. The modular electrode array of claim 1 comprising an electronic subsystem electrically coupled to the at least two first and second proximal conductive interconnect ends, and wherein the electronic subsystem is configured to transfer sensed electrical signals from the at least two first and second electrodes and respective conductive interconnects to at least one electrically conductive lead.

13. The modular electrode array of claim 12, wherein there are a plurality of first and second electrodes electrically connected to respective conductive interconnects comprising a plurality of conductive traces, and wherein the number of electrically conductive leads is less than the number of conductive traces, and wherein the electronic subsystem includes a multiplexer circuit configured to selectively transfer signals from a subset of the plurality of first and second electrodes and respective plurality of conductive traces to the electrically conductive leads.

14. The modular electrode array of claim 12, wherein the electronic subsystem includes a noise reduction circuit.

15. The modular electrode array of claim 12, including a recording system electrically coupled to the at least one electrically conductive lead.

16. The modular electrode array of claim 1 wherein the longitudinal axis of the first connector substrate is substantially aligned perpendicular to the first and second pitch lengths.

17. The modular electrode array of claim 1 wherein there are X by Y electrode modules connected by intermediate connector substrates with X by Y conductive interconnects electrically connected to at least two electrodes supported on the respective flexible substrates, and wherein X and Y are positive integers.

18. The modular electrode array of claim 1 wherein:
a) a first width where the first connector end connects to the first perimeter is less than the first pitch length between the at least two first electrodes supported on the first substrate, and
b) wherein a second width where the second connector end of the first connector substrate connects to the second perimeter is less than the second pitch length between the at least two second electrodes supported on the second substrate.

19. The modular electrode array of claim 1 wherein:
a) the at least two first electrodes are aligned along a second axis;

b) the at least two second electrodes are aligned along a third axis; and
c) the first longitudinal axis is substantially perpendicular to the second and third axes of the respective at least two first and second electrodes.

20. The modular electrode array of claim 1 wherein the backing has a backing perimeter that extends laterally out beyond the respective first and second perimeters of the first and second substrates.

21. The modular electrode array of claim 1 wherein at least one of the first and second substrates is comprised of a polymeric material selected from the group consisting of parylene and polyimide, and wherein the backing comprises silicone.

22. A modular electrode array, comprising:
 a) a first electrode module, comprising:
  i) a first flexible substrate comprising a first perimeter; and
  ii) a plurality of first electrodes supported on a first side of the first substrate,
  iii) wherein at least two of the plurality of first electrodes are spaced apart from each other by a first pitch length of the first substrate;
 b) a second electrode module, comprising:
  i) a second flexible substrate comprising a second perimeter; and
  ii) a plurality of second electrodes supported on a first side of the second substrate,
  iii) wherein at least two of the plurality of second electrodes are spaced apart from each other by a second pitch length of the second substrate;
 c) a connector substrate extending along a longitudinal axis from a first connector end to a second connector end, wherein:
  i) the first connector end is connected to the first substrate perimeter of the first electrode module and the second connector end is connected to the second substrate perimeter of the second electrode module, and
  ii) wherein a first width where the first connector end connects to the first perimeter is less than the first pitch length between the at least two first electrodes supported on the first substrate, and
  iii) wherein a second width where the second connector end of the first connector substrate connects to the second perimeter is less than the second pitch length between the at least two second electrodes supported on the second substrate, and
  iv) wherein the longitudinal axis of the first connector substrate intersects both the first pitch between and spaced from the two first electrodes and the second pitch between and spaced from the two second electrodes;
 d) a plurality of first conductive interconnects and a plurality of second conductive interconnects, each of the first and second conductive interconnect extending from a proximal interconnect end to a distal interconnect end,
  i) wherein the proximal first and second interconnect ends are configured for electrical connection to an external electrical device, and
  ii) wherein the distal interconnect ends of the first conductive interconnects are supported by the first flexible substrate and electrically coupled to a respective one of the plurality of first electrodes, and
  iii) wherein the distal interconnect ends of the second conductive interconnects are supported by the first flexible substrate, the connector substrate, and the second flexible substrate and electrically coupled to a respective one of the plurality of second electrodes; and
 e) a backing supporting the first and second substrates and the intermediate first connector substrate on respective second sides thereof opposite the first sides to thereby maintain the spatial separation between the first and second modules.

23. The modular electrode array of claim 22 wherein the longitudinal axis of the connection substrate is substantially aligned perpendicular to the first and second pitch lengths.

24. The modular electrode array of claim 22, further comprising:
 a) a third electrode module, comprising:
  i) a third flexible substrate comprising a third perimeter; and
  ii) a plurality of third electrodes supported on a first side of the third substrate,
  iii) wherein at least two of the plurality of third electrodes are spaced apart from each other by a third pitch length of the third substrate;
 b) a second connector substrate extending along a second longitudinal axis from a third connector end to a fourth connector end, wherein:
  i) the third connector end is connected to the second substrate perimeter and the fourth connector end is connected to the third substrate perimeter, and
  ii) wherein a third width where the third connector end connects to the second perimeter is less than the second pitch length between the at least two second electrodes supported on the second substrate, and
  iii) wherein a fourth width where the fourth connector end of the second connector substrate connects to the third perimeter is less than the third pitch length between the at least two third electrodes supported on the third substrate; and
  iv) wherein the second longitudinal axis of the second connector substrate intersects both the second pitch between and spaced from the two second electrodes and the third pitch between and spaced from the two second electrodes, and
 c) at least two third conductive interconnects, each extending from a proximal interconnect end to a distal interconnect portion having a distal interconnect end,
  i) wherein the proximal third interconnect ends are configured for electrical connection to the external electrical device, and
  ii) wherein the distal portions of the third conductive interconnects are supported by the first flexible substrate, the first connector substrate, the second flexible substrate, the second connector substrate, and the third flexible substrate with the third distal interconnect ends electrically coupled to respective ones of the at least two third electrodes; and
 d) wherein the backing supports the first, second and third substrates and the intermediate first and second connector substrates on respective second sides thereof opposite the first sides to thereby maintain the spatial separation between the first, second and third modules.

25. The modular electrode array of claim 24, further comprising:
 a) a fourth electrode module, comprising:
  i) a fourth flexible substrate comprising a fourth perimeter; and
  ii) a plurality of fourth electrodes supported on a first side of the fourth substrate, iii) wherein at least two of the plurality of fourth electrodes are spaced apart from each other by a fourth pitch of the fourth substrate;
b) a third connector substrate extending along a third longitudinal axis from a fifth connector end to a sixth connector end, wherein:
i) the fifth connector end is connected to the third substrate perimeter and the sixth connector end is connected to the fourth substrate perimeter, and
ii) wherein a fifth width where the fifth connector end connects to the third perimeter is less than the third pitch length between the at least two third electrodes supported on the third substrate, and
iii) wherein a sixth width where the sixth connector end of the third connector substrate connects to the fourth perimeter is less than the fourth pitch length between the at least two fourth electrodes supported on the fourth substrate, and
iv) wherein the third longitudinal axis of the third connector substrate intersects both the third pitch between and spaced from the two third electrodes and the fourth pitch between and spaced from the two fourth electrodes; and
c) at least two fourth conductive interconnects, each extending from a proximal interconnect end to a distal interconnect portion having a distal interconnect end,
i) wherein the proximal fourth interconnect ends are configured for electrical connection to the external electrical device, and
ii) wherein the distal portions of the fourth conductive interconnects are supported by the first flexible substrate, the first connector substrate, the second flexible substrate, the second connector substrate, the third flexible substrate, the third connector substrate, and the fourth flexible substrate with the fourth distal interconnect ends electrically coupled to respective ones of the at least two fourth electrodes,
d) wherein the backing supports the first, second, third and fourth substrates and the intermediate first, second and third connector substrates on respective second sides thereof opposite the first sides to thereby maintain the spatial separation between the first, second, third and fourth modules.

26. The modular electrode array of claim 22 wherein at least one of the first and second substrates is comprised of a polymeric material selected from the group consisting of parylene and polyimide, and wherein the backing is comprised of silicone.

27. A modular electrode array, comprising:
a) a first electrode module, comprising:
i) a first flexible substrate comprising a first perimeter; and
ii) at least two first electrodes supported on the first substrate,
iii) wherein the at least two first electrodes are spaced apart from each other by a first pitch;
b) a second electrode module, comprising:
i) a second flexible substrate comprising a second perimeter; and
ii) at least two second electrodes supported on the second substrate,
iii) wherein the at least two second electrodes are spaced apart from each other by a second pitch;
c) a first connector substrate extending from a first connector end to a second connector end, wherein:
i) the first connector end is connected to the first substrate perimeter and the second connector end is connected to the second substrate perimeter, and
ii) wherein a first width where the first connector end connects to the first perimeter is less than the first pitch between the at least two first electrodes supported on the first substrate, and
iii) wherein a second width where the second connector end of the first connector substrate connects to the second perimeter is less than the second pitch between the at least two second electrodes supported on the second substrate; and
d) at least two first conductive interconnects and at least two second conductive interconnects, each of the first and second conductive interconnects extending from a proximal interconnect end to a distal interconnect portion having a distal interconnect end,
i) wherein the proximal first and second interconnect ends are configured for electrical connection to an external electrical device, and
ii) wherein the distal portions of the first conductive interconnects are supported by the first flexible substrate with the first distal interconnect ends electrically coupled to respective ones of the at least two first electrodes, and
iii) wherein the distal portions of the second conductive interconnects are supported by the first flexible substrate, the first connector substrate, and the second flexible substrate with the second distal interconnect ends electrically coupled to respective ones of the at least two second electrodes; and
e) an aperture extending through at least one of the respective first and second flexible substrates of the first and second electrode modules; and
f) a wave guide configured to deliver light to the at least one aperture.

28. A modular electrode array, comprising:
a) a first electrode module, comprising:
i) a first flexible substrate comprising a first perimeter; and
ii) at least two first electrodes supported on the first substrate,
iii) wherein the at least two first electrodes are spaced apart from each other by a first pitch;
b) a second electrode module, comprising:
i) a second flexible substrate comprising a second perimeter; and
ii) at least two second electrodes supported on the second substrate,
iii) wherein the at least two second electrodes are spaced apart from each other by a second pitch;
c) wherein at least one of the two first and second electrodes is a penetrating electrode;
d) a first connector substrate extending from a first connector end to a second connector end, wherein:
i) the first connector end is connected to the first substrate perimeter and the second connector end is connected to the second substrate perimeter, and
ii) wherein a first width where the first connector end connects to the first perimeter is less than the first pitch between the at least two first electrodes supported on the first substrate, and
iii) wherein a second width where the second connector end of the first connector substrate connects to the second perimeter is less than the second pitch between the at least two second electrodes supported on the second substrate; and e) at least two first conductive interconnects and at least two second conductive interconnects, each of the first and second conductive interconnects extending from a proximal interconnect end to a distal interconnect portion having a distal interconnect end,
   i) wherein the proximal first and second interconnect ends are configured for electrical connection to an external electrical device, and
   ii) wherein the distal portions of the first conductive interconnects are supported by the first flexible substrate with the first distal interconnect ends electrically coupled to respective ones of the at least two first electrodes, and
   iii) wherein the distal portions of the second conductive interconnects are supported by the first flexible substrate, the first connector substrate, and the second flexible substrate with the second distal interconnect ends electrically coupled to respective ones of the at least two second electrodes.

29. A modular electrode array, comprising:
a) a first electrode module, comprising:
   i) a first flexible substrate comprising a first perimeter; and
   ii) at least one first electrode supported on a first side of the first substrate;
b) a second electrode module, comprising:
   i) a second flexible substrate comprising a second perimeter; and
   ii) at least one second electrode supported on a first side of the second substrate;
c) a first connector substrate extending from a first connector end to a second connector end, wherein the first connector end is connected to the first substrate perimeter and the second connector end is connected to the second substrate perimeter to thereby provide a spatial separation between the first and second modules;
d) at least one first conductive interconnect and at least one second conductive interconnect, the first and second conductive interconnects extending from a proximal interconnect end to a distal interconnect portion having a distal interconnect end,
   i) wherein the proximal first and second interconnect ends are configured for electrical connection to an external electrical device, and
   ii) wherein the distal portion of the first conductive interconnect is supported by the first flexible substrate with the first distal interconnect end electrically coupled to the at least one first electrode, and
   iii) wherein the distal portion of the second conductive interconnect is supported by the first flexible substrate, the first connector substrate, and the second flexible substrate with the second distal interconnect end electrically coupled to the at least one second electrode; and
e) a backing supporting the first and second substrates and the intermediate first connector substrate on respective second sides thereof opposite the first sides to thereby maintain the spatial separation between the first and second modules.

30. The modular electrode array of claim 29 wherein at least one of the first and second substrates is comprised of a polymeric material selected from the group consisting of parylene and polyimide.

31. The modular electrode array of claim 29 wherein the backing comprises silicone.

32. A method for forming a modular electrode array, comprising the steps of:
a) disposing at least two first electrodes on a first side of a first flexible substrate having a first perimeter to form a first electrode module, wherein the at least two first electrodes are spaced apart from each other by a first pitch length;
b) disposing at least two second electrodes on a first side of a second flexible substrate having a second perimeter to form a second electrode module, wherein the at least two second electrodes are spaced apart from each other by a second pitch length;
c) providing a connector substrate extending along a longitudinal axis from a first connector end to a second connector end with the first connector end connected to the first substrate perimeter and the second connector end connected to the second substrate perimeter to thereby provide a spatial separation between the first and second modules; and
d) attaching a backing to the first and second substrates and the intermediate first connector substrate on respective second sides thereof opposite the first sides to thereby maintain the spatial separation between the first and second modules,
e) wherein the longitudinal axis of the first connector substrate intersects both the first pitch length between and spaced from the two first electrodes and the second pitch length between and spaced from the two second electrodes; and
f) providing at least two first conductive interconnects and at least two second conductive interconnects, each interconnect extending from a proximal interconnect end to a distal interconnect portion having a distal interconnect end,
   i) wherein the proximal first and second interconnect ends are configured for electrical connection to an external electrical device, and
   ii) wherein the distal portions of the first conductive interconnects are supported by the first flexible substrate with the first distal interconnect, ends electrically coupled to respective ones of the at least two first electrodes, and
   iii) wherein the distal portions of the second conductive interconnects are supported by the first flexible substrate, the connector substrate, and the second flexible substrate with the second distal interconnect ends electrically coupled to respective ones of the at least two second electrodes.

33. The method of claim 32, including:
a) forming a plurality of X times Y electrode modules; and
b) connecting adjacent modules to each other with respective connector substrates and conductive interconnects to thereby form an X by Y modular electrode array, wherein X and Y are positive integers.

34. The method of claim 33, wherein X=Y.

35. The method of claim 32, wherein attaching the backing includes injection molding a silicone backing and attaching the first and second flexible substrates to the silicone backing.

36. The method of claim 32, wherein attaching the backing includes adhering a thin-film backing to the first and second flexible substrates.

37. The method of claim 32, including providing at least one of the two first and second conductive interconnects comprising a conductive trace arranged in a serpentine pattern.

38. The method of claim 32, including providing a plurality of first and second conductive interconnects electrically connected to respective ones of a plurality of first and second electrodes and further providing the plurality of conductive interconnects comprising at least one group of helically coiled conductive traces.

39. The method of claim 38, wherein providing the at least one group of helically coiled conductive traces includes helically coiling the conductive traces around a tube comprising a flexible material.

40. The method of claim 32, including forming at least one aperture in at least one of the first and second flexible substrates of the respective first and second electrode modules.

41. The method of claim 32 including providing:
a) a first width where the first connector end connects to the first perimeter being less than the first pitch length between the at least two first electrodes supported on the first substrate, and
b) a second width where the second connector end of the connector substrate connects to the second perimeter being less than the second pitch length between the at least two second electrodes supported on the second substrate.

42. The method of claim 32 including providing:
a) the at least two first electrodes being aligned along a second axis;
b) the at least two second electrodes being aligned along a third axis; and
c) the first longitudinal axis being substantially perpendicular to the second and third axes of the respective at least two first and second electrodes.

43. The method of claim 32 including forming at least one of the first and second substrates of a polymeric material selected from the group consisting of parylene and polyimide, and forming the backing of silicone.

* * * * *

UNITED STATES PATENT AND TRADEMARK OFFICE
CERTIFICATE OF CORRECTION

PATENT NO. : 9,248,269 B2  Page 1 of 1
APPLICATION NO. : 13/556715
DATED : February 2, 2016
INVENTOR(S) : Daryl R. Kipke et al.

It is certified that error appears in the above-identified patent and that said Letters Patent is hereby corrected as shown below:

In the claims,

Column 11, line 59 (Claim 4, line 1) after the word "array" insert the word --of--

Column 18, line 39 (Claim 32, line 40) after the word "interconnect" delete the ","

Signed and Sealed this
Nineteenth Day of July, 2016

Michelle K. Lee
*Director of the United States Patent and Trademark Office*